US00PP37463P2

(12) United States Plant Patent
Li

(10) Patent No.: US PP37,463 P2
(45) Date of Patent: Jun. 9, 2026

(54) ***VERBENA* PLANT NAMED 'KLEVP24151'**

(50) Latin Name: ***Verbena* x *hybrida***
Varietal Denomination: KLEVP24151

(71) Applicant: KLEMM + SOHN GMBH & CO. KG, Stuttgart (DE)

(72) Inventor: Ruijun Li, North Parramatta (AU)

(73) Assignee: Klemm + Sohn GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/237,783

(22) Filed: Jun. 13, 2025

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 5/00; A01H 6/86
See application file for complete search history.

(56) References Cited

PUBLICATIONS

Selecta-Annuals 2025 Spring Annuals Trixi 2024/2025, retrieved on Sep. 15, 2025 at https://josvainiugeles.lt/wp-content/uploads/2024/09/Selecta-Annuals-2025.pdf, pp. 1-3, 104-105, 170-171 (4 pp. total). (Year: 2025).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Verbena* plant particularly distinguished by large, red flowers, with small, white eyes and a semi-upright growth habit, is disclosed.

1 Drawing Sheet

Genus and species: *Verbena* x *hybrida*.
Variety denomination: 'KLEVP24151'.

BACKGROUND OF THE NEW PLANT

The present invention comprises a new and distinct variety of *Verbena*, botanically known as *Verbena* x *hybrida*, and hereinafter referred to by the variety name 'KLEVP24151'. 'KLEVP24151' originated from a cross-pollination conducted in October 2019 in Cobbitty, New South Wales, Australia between the proprietary female *Verbena* variety '16.60.82' (unpatented), and the proprietary male *Verbena* variety '10.00.67' (unpatented).

The seeds from the cross were sown and plants were grown for evaluation, where an individual plant designated 'KLEVP24151' was selected from the group of plants in Cobbitty, New South Wales, Australia in October 2019.

In October 2019, 'KLEVP24151' was first vegetatively propagated by vegetative cuttings in Cobbitty, New South Wales, Australia. 'KLEVP24151' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Large, red flowers with small, white eyes, and
2. Semi-upright growth habit.

DESCRIPTION OF THE PHOTOGRAPH

This new *Verbena* plant is illustrated by the accompanying photograph which shows the plant's overall plant habit including form, foliage, and flowers. The photograph is of a plant approximately 11-weeks-old grown indoors in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLEVP24151'. The data which define these characteristics were collected from asexual reproductions carried out in Cobbitty, New South Wales, Australia. Data was collected on three-month-old plants grown in 2021. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP24151'.

Parentage:
- *Female parent*.—'16.60.82' (unpatented).
- *Male parent*.—'10.00.67' (unpatented).

Plant:
- *Growth and branching habit*.—Semi-upright.
- *Height* (*from top of soil*).—32.0 cm.
- *Width* (*horizontal plant diameter*).—42.5 cm.
- *Time to produce a finished flowering plant*.—Approximately 8 weeks.
- *Time to initiate and develop roots*.—Approximately 2 weeks.

*Root description*.—RHS 155B (White), fine fibrous roots.

Stems:

*Number of branches per plant*.—Approximately 25.

*Length*.—20.5 cm.

*Diameter*.—0.26 cm.

*Internode length*.—2.3 cm.

*Color*.—RHS 139D.

*Anthocyanin*.—Absent.

*Texture and appearance*.—Pubescent, round.

Leaves:

*Arrangement*.—Opposite.

*Immature and mature leaf*.—Color: Upper surface: RHS 141A. Lower surface: RHS 141C.

*Length*.—2.5 cm.

*Width*.—1.4 cm.

*Shape*.—Lanceolate.

*Apex*.—Acute.

*Base*.—Obtuse.

*Margin*.—Crenate.

*Texture*.—Upper surface: Leathery. Lower surface: Rugose.

*Anthocyanin on leaf upper surface*.—Absent.

*Venation type*.—Pinnate.

*Venation color*.—Upper surface: RHS 141D. Lower surface: RHS 141D.

*Petioles*.—Length: 0.2 cm. Diameter: 0.1 cm. Color: RHS 141D. Texture: Leathery.

Flower buds:

*Shape*.—Tall, cylindrical.

*Length*.—0.6 cm.

*Diameter*.—0.2 cm.

*Color* (*at tight bud*).—RHS 141D.

Inflorescence:

*Blooming habit* (*flowering season*).—Continuously.

*Lastingness of individual blooms on the plant*.—One week.

*Fragrance*.—Absent.

*Inflorescence type*.—Umbel.

*Length of inflorescence*.—4.7 cm.

*Diameter of inflorescence*.—6.2 cm.

*Shape of inflorescence when viewed from the side*.—Broad obovate.

*Number of florets per inflorescence*.—21.

*Peduncle*.—Color: RHS 141D. Length: 2.2 cm. Diameter: 0.1 cm. Surface texture: Pubescent.

Florets:

*Length*.—2.3 cm.

*Diameter*.—1.9 cm.

*Upper surface texture*.—Smooth.

*Form*.—Single.

*Color*.—Immature: Upper surface: RHS 42A with white eyes RHS 155B. Lower surface: RHS 44D with white eyes RHS 155B. Mature: Upper surface: RHS 44A with white eyes RHS 155B. Lower surface: RHS 44D with white eyes RHS 155B.

*Corolla tube length*.—1.6 cm.

*Corolla outer tube color*.—RHS 141A.

*Corolla lobes arrangement*.—Free.

*Corolla curvature of longitudinal axis*.—Straight.

*Corolla undulation of margin*.—Weak.

*Corolla eye diameter size*.—Small.

*Petals*.—Length of lobe: 1.6 cm. Diameter of lobe: 2.1 cm. Lobe shape: Reniform. Apex: Emarginate. Base: Fused forming a tube. Margin: Entire. Texture: Upper surface: Glossy, satiny. Lower surface: Glossy, satiny.

*Pedicels*.—Not visible.

Sepals:

*Shape*.—Lanceolate but fused.

*Apex*.—Acute.

*Margin*.—Entire.

*Length*.—1.2 cm.

*Diameter*.—0.2 cm.

*Color*.—RHS 141C.

*Texture*.—Upper surface: Hairy, dull. Lower surface: Hairy, dull.

*Calyx anthocyanin*.—Absent.

Reproductive organs:

*Stamens*.—Present.

*Quantity*.—4.

*Appearance*.—Shiny.

*Color*.—RHS 139D.

*Filament length*.—0.3 cm.

*Filament diameter*.—0.1 cm.

*Anther*.—Shape: Elliptic. Color: RHS 141D. Length: 0.2 cm. Diameter: 0.1 cm.

*Pollen amount*.—Sparse.

*Pistils*.—Number: 1. Length: 1.1 cm. Diameter: 0.1 cm.

*Stigma*.—Color: RHS 141D. Appearance: Ovate. Length: 0.2 cm. Diameter: 0.1 cm.

*Style*.—Color: RHS 141D. Length: 0.9 cm. Diameter: 0.1 cm. Appearance: Long.

Fruit and seed set: To date, fruit and seed development have not been observed on plants.

Disease and pest/insect resistance: Plants of KLEVP24151 have been observed to be good tolerate to powdery mildew (*Podosphaera xanthii*).

COMPARISON WITH PARENTAL LINES AND KNOWN VARIETY

'KLEVP24151' is distinguished from its parents as described in Table 1.

TABLE 1

Comparison with Parental Lines

| Trait | Variety 'KLEVP24151' | Female parent '16.60.82' | Male Parent '10.00.67' |
|---|---|---|---|
| Flower color | Red with white eyes | Magenta with white eyes | Red |

'KLEVP24151' is most similar to the commercial *Verbena* variety Lascar Red Rose 'KLEVP11419' (U.S. Plant Pat. No. 24,031). Differences between the varieties are described in Table 2.

TABLE 2

| Comparison with Similar Variety | | |
|---|---|---|
| Trait | Variety 'KLEVP24151' | Commercial line Lascar Red Rose |
| Eye size | Smaller than Lascar Red Rose | Bigger than 'KLEVP24151' |

TABLE 2-continued

| Comparison with Similar Variety | | |
|---|---|---|
| Trait | Variety 'KLEVP24151' | Commercial line Lascar Red Rose |
| Flower size | Bigger than Lascar Red Rose | Smaller than 'KLEVP24151' |

I claim:

1. A new and distinct variety of *Verbena* plant designated 'KLEVP24151' as illustrated and described herein.

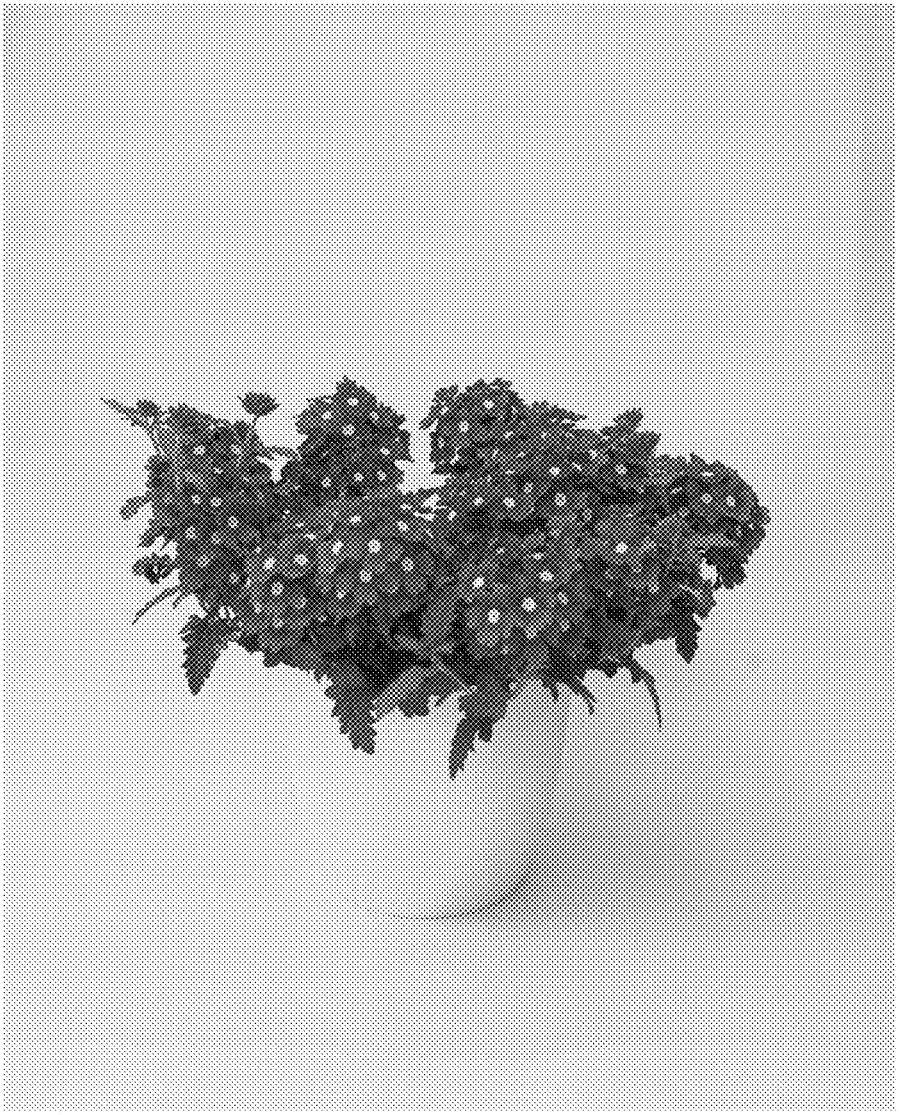

* * * * *